US012700421B1

(12) United States Patent
Reiter et al.

(10) Patent No.: US 12,700,421 B1
(45) Date of Patent: Aug. 4, 2026

(54) PREDICTING CLINICALLY MEANINGFUL CHANGES IN BEHAVIORAL HEALTH SYMPTOMATOLOGY USING PATIENT VOICE INPUTS

(71) Applicant: Verily Health Inc., Dallas, TX (US)

(72) Inventors: Jacob Reiter, San Francisco, CA (US); Joel Shor, Cambridge, MA (US); Natalie Lester, Columbus, OH (US); Stefanie Nickels, Westford, MA (US); Weston Ferrer, San Francisco, CA (US); Wen-sheng Tseng, Boston, MA (US); Jordan Tharp, Oakland, CA (US)

(73) Assignee: Verily Health Inc., Dallas, TX (US)

( * ) Notice: Subject to any disclaimer, the term of this patent is extended or adjusted under 35 U.S.C. 154(b) by 25 days.

(21) Appl. No.: 18/394,506

(22) Filed: Dec. 22, 2023

Related U.S. Application Data

(60) Provisional application No. 63/477,898, filed on Dec. 30, 2022.

(51) Int. Cl.
| | |
|---|---|
| *G10L 25/66* | (2013.01) |
| *G10L 25/63* | (2013.01) |
| *G16H 50/20* | (2018.01) |

(52) U.S. Cl.
CPC .............. *G10L 25/66* (2013.01); *G10L 25/63* (2013.01); *G16H 50/20* (2018.01)

(58) Field of Classification Search
CPC .......... G10L 25/66; G10L 25/63; G16H 50/20

USPC .......................................... 704/231–232, 246
See application file for complete search history.

(56) References Cited

U.S. PATENT DOCUMENTS

| | | | |
|---|---|---|---|
| 10,748,644 | B2 | 8/2020 | Shriberg et al. |
| 11,120,895 | B2 | 9/2021 | Shriberg et al. |
| 2008/0234558 | A1 | 9/2008 | Kumar et al. |
| 2018/0322961 | A1 | 11/2018 | Kim et al. |
| 2019/0341152 | A1 | 11/2019 | Mellem et al. |
| 2020/0121236 | A1 | 4/2020 | Gao et al. |
| 2022/0328064 | A1 | 10/2022 | Shriberg et al. |

*Primary Examiner* — George C Monikang
(74) *Attorney, Agent, or Firm* — Kilpatrick Townsend & Stockton LLP

(57) ABSTRACT

One example method for predicting clinically meaningful changes in behavioral health symptomatology using patient voice inputs includes receiving a baseline behavioral sample indicating an initial behavioral health symptomatology of an individual; receiving a subsequent behavioral sample including a supplemental voice recording from the individual; computing a difference score from a trained machine-learning ("ML") model by providing the baseline behavioral sample and the subsequent behavioral sample as input to the trained ML model wherein the difference score indicates a predicted change in behavioral health symptomatology of the individual, the trained ML model being configured to output a score indicating a predicted change in behavioral health symptomatology based on input data; and outputting the predicted change in behavioral health symptomatology to a client device executing a graphical user interface indicating the change for an entity treating the individual.

20 Claims, 7 Drawing Sheets

400

402b

404b

Overall Score: 8

406b

First subfactor:      Moderate (+1.8)
Second subfactor:     Low (+0.3)
Third subfactor:      Low (+0.1)
Fourth subfactor:     High (+5.6)

408c

Digital Journey
Rediscovering
meaning in old joys

408d

Digital Journey
Working on
concentration

PREDICTING CLINICALLY MEANINGFUL CHANGES IN BEHAVIORAL HEALTH SYMPTOMATOLOGY USING PATIENT VOICE INPUTS

CROSS REFERENCE TO RELATED APPLICATION(S)

This application is a Nonprovisional of and claims priority to U.S. Provisional Application No. 63/477,898, filed Dec. 30, 2022, and titled "Predicting Clinically Meaningful Changes In Behavioral Health Symptomatology Using Patient Voice Inputs," the contents of which are herein incorporated in its entirety.

FIELD

The present application generally relates to predicting behavioral health symptomatology using machine learning and more particularly relates to predicting clinically meaningful changes in behavioral health symptomatology using patient voice inputs.

BACKGROUND

Diagnosing and monitoring patients with behavioral health disorders can be difficult for both patients and behavioral health professionals. Patients undergoing monitoring or treatment for a behavioral health disorder may be required to regularly undergo testing or take assessments to provide diagnostic information for a behavioral health professional. In addition, monitoring patients over time can be difficult for behavioral health professionals because patients may not always keep appointments, may not perform all requested assessments or tests, or may be difficult to contact.

SUMMARY

Various examples are described for predicting clinically meaningful changes in behavioral health symptomatology using patient voice inputs. One example method for predicting clinically meaningful changes in behavioral health symptomatology using patient voice inputs includes receiving a baseline behavioral sample indicating an initial behavioral health symptomatology of an individual; receiving a subsequent behavioral sample including a supplemental voice recording from the individual; computing a difference score from a trained machine-learning ("ML") model by providing the baseline behavioral sample and the subsequent behavioral sample as input to the trained ML model wherein the difference score indicates a predicted change in behavioral health symptomatology of the individual, the trained ML model being configured to output a score indicating a predicted change in behavioral health symptomatology based on input data; and outputting the predicted change in behavioral health symptomatology to a client device executing a graphical user interface indicating the change for an entity treating the individual.

One example system includes one or more processors; and a non-transitory computer-readable medium comprising program code that is executable by the one or more processors to receive a baseline behavioral sample indicating an initial behavioral health symptomatology of an individual; receive a subsequent behavioral sample including a supplemental voice recording from the individual; compute a difference score from a trained machine-learning ("ML") model by providing the baseline behavioral sample and the subsequent behavioral sample as input to the trained ML model wherein the difference score indicates a predicted change in behavioral health symptomatology of the individual, the trained ML model being configured to output a score indicating a predicted change in behavioral health symptomatology based on input data; and output the predicted change in behavioral health symptomatology to a client device executing a graphical user interface indicating the change for an entity treating the individual.

One example non-transitory computer-readable medium comprising program code that is executable by one or more processors to receive a baseline behavioral sample indicating an initial behavioral health symptomatology of an individual; receive a subsequent behavioral sample including a supplemental voice recording from the individual; compute a difference score from a trained machine-learning ("ML") model by providing the baseline behavioral sample and the subsequent behavioral sample as input to the trained ML model wherein the difference score indicates a predicted change in behavioral health symptomatology of the individual, the trained ML model being configured to output a score indicating a predicted change in behavioral health symptomatology based on input data; and output the predicted change in behavioral health symptomatology to a client device executing a graphical user interface indicating the change for an entity treating the individual.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
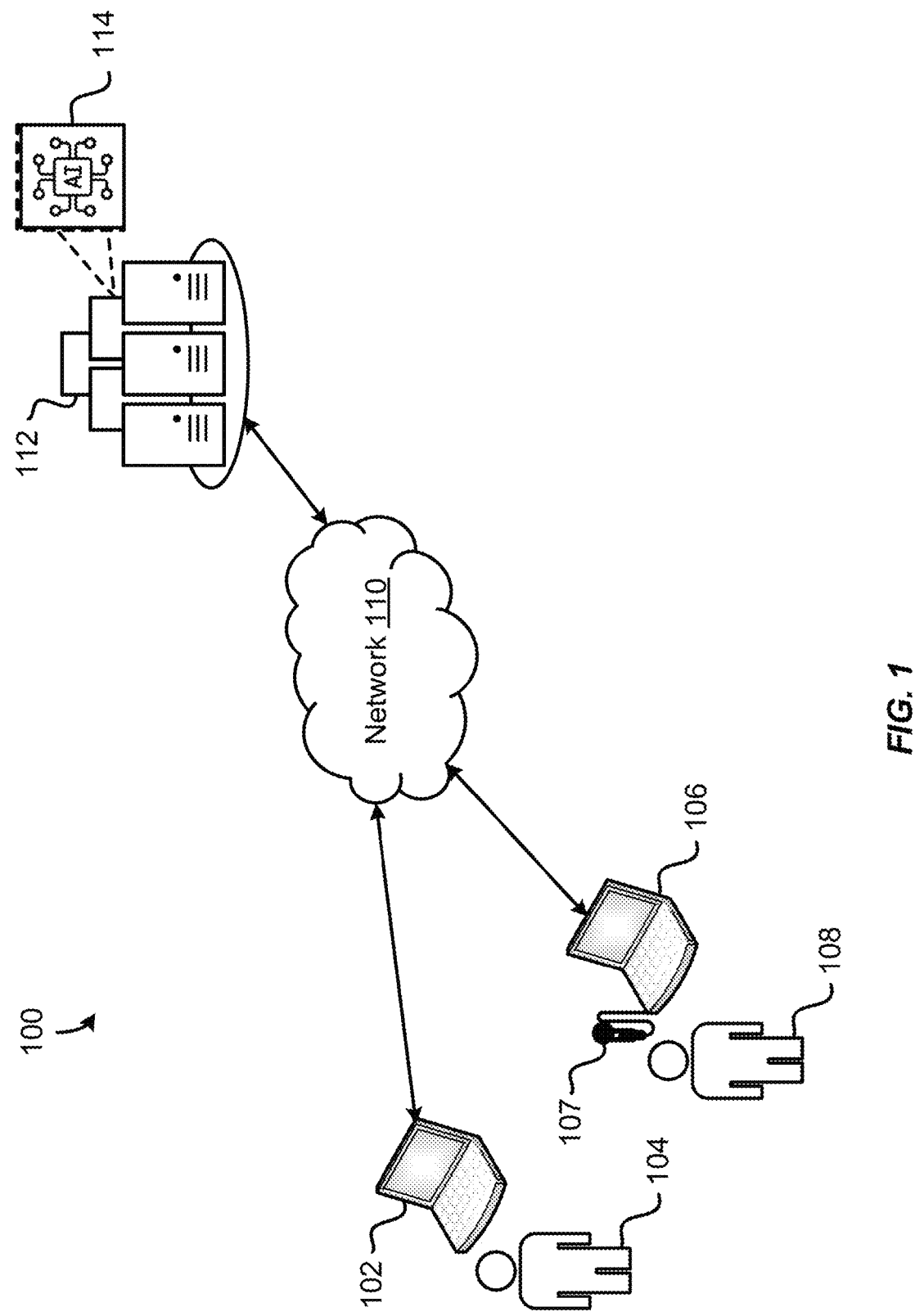
FIG. 1 shows an example system for predicting clinically meaningful changes in behavioral health symptomatology using patient voice inputs.

Examples are described herein in the context of predicting clinically meaningful changes in behavioral health symptomatology using patient voice inputs. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Diagnosing and monitoring patients with behavioral health disorders, like depression, can be challenging for behavioral health professionals and a burden for the patients. Conventional techniques involve clinical visits with the patient and patients repeatedly taking assessment questionnaires. For example, behavioral health disorders, such as major depressive disorder and anxiety, have corresponding diagnostic tests that patients can take that can be used to help diagnose their condition as well as its severity. However, repeatedly taking and scoring the assessment can be burdensome on both the patient and the behavioral health professional. To help reduce the burden on the patient as well as the behavioral health providers, assessing behavioral health disorders may instead be performed by analyzing voice inputs obtained from one or more patients.

For example, in the case of a patient suspected of having or who has already been diagnosed with major depressive disorder, the patient will typically be asked to complete a written assessment referred to as Patient Health Questionnaire 9, or PHQ-9. The assessment includes nine questions with corresponding scores from 0-3. The scores for each of the questions are then added together to provide a composite score that provides an assessment of whether the patient is depressed and the severity of depression. For a patient undergoing treatment for chronic depression, they may periodically re-take the PHQ-9 exam and work with a behavioral health professional to manage their depression.

However, instead of repeatedly taking the PHQ-9 assessment, a patient may take the PHQ-9 assessment and also capture a behavioral sample, which can be a capture of any type of behavioral data such as a voice, video or multimedia recording, which may only be a few minutes long and may only record the patient discussing their day or issues they are facing in their lives. The combination of these two data points may establish an initial baseline behavioral sample for the patient's behavioral health symptomatology.

Subsequently, the patient may record additional behavioral samples that may be used to detect changes in their behavioral health symptomatology over time. As with the baseline behavioral sample, the additional (or supplemental) behavioral samples may only be thirty seconds to a few minutes long, though the patient does not take another assessment. Additionally, the behavioral samples may be recorded by the patient's own user device, such as a smartphone or tablet, without also meeting with a behavioral health professional. These behavioral samples are then sent to a remote or cloud computer system for analysis.

The cloud computer system will receive the behavioral sample and access the patient's baseline PHQ-9 score and baseline voice input. These three items will then be inputted to a machine learning ("ML") model that has been trained to analyze behavioral samples and evaluate potential changes in the patient's behavioral health symptomatology. Thus, based on an individual voice or video input, the ML model can provide an assessment of whether the patient's depression has improved, worsened, or is unchanged.

To monitor the patient's depression over time, additional supplemental assessments based on supplemental behavioral samples and the baseline behavioral sample may be performed to determine whether the depression is improving, worsening, or remaining relatively constant. These supplemental assessments may continue over time and, as the progression worsens or improves, information about the change over time may be provided to a health care professional that is working with the patient. In addition, in some cases, the cloud system may suggest interventions to the health care professional based on the detected changes from the baseline behavioral sample.

However, over time, the baseline behavioral sample may no longer be an accurate baseline. This may be due to changes in the patient's behavioral health or due to the amount of time that has passed since the last baseline behavioral sample was obtained. Thus, the cloud system may determine whether the baseline behavioral sample should be replaced with a new baseline behavioral sample and, if so, it may prompt the user to re-take the PHQ-9 assessment and record a new input as the basis for resetting the baseline behavioral sample. Once the new baseline behavioral sample is received, the cloud system may then analyze subsequent supplemental behavioral samples with the new baseline behavioral sample.

And while this example discusses the use of a single model for assessing a patient's behavioral health, another example may employ multiple models. For example, rather than a single ML model, the cloud server may run nine separate ML models, each trained to determine a change for one of the nine questions within the PHQ-9 assessment. Thus, each individual ML model outputs a score for one of the PHQ-9 assessment categories, which may be used to provide a more granular assessment of any changes over time from the baseline.

Still further information may be obtained from the assessments, such as subfactors correlating to different aspects of the PHQ-9 assessment. For example, depending on the ML model's output, the system may identify one or more subfactors, such as sleep and appetite or anhedonia and depressed mood, in which significant changes occurred and other subfactors where no significant change was detected. By further identifying these subfactors, the cloud server may be able to identify more targeted interventions for the patient, rather than a more generalized assessment based on the total predicted PHQ-9 score.

Such a system may allow a user to provide useful diagnostic information to a behavioral health system without performing a formalized assessment or attending a clinical visit. Instead, the patient may be requested to provide a voice input periodically over time, e.g., once or twice a week, which can be analyzed by the corresponding ML model(s). Depending on the results of the analysis, interventions may be recommended to a behavioral health professional or an indication that no significant change has been detected. For some interventions, the engagement between the behavioral health professional and the patient may occur entirely via online interactions, such as using direct messaging. By providing such information from the automated assessment, the burden on the behavioral health professional may be lessened and they may be able to quickly identify on patients with serious symptomatologies, while monitoring patients with more moderate or mild behavioral health disorders and selecting or approving suggested interventions from the cloud server.

This illustrative example is given to introduce the reader to the general subject matter discussed herein and the disclosure is not limited to this example. The following sections describe various additional non-limiting examples and examples of predicting clinically meaningful changes in behavioral health symptomatology using patient voice inputs.

Referring now to FIG. 1, FIG. 1 shows an example system for predicting clinically meaningful changes ("CMC") in behavioral health symptomatologies using patient voice inputs. The example system includes two user devices 102, 106 and a remote cloud server system 112. These components are communicatively connected to each other via one or more intervening networks, collectively illustrated as network 110. The intervening networks may include the internet or any other suitable networks that may include any local area network ("LAN"), metro area network ("MAN"), wide area network ("WAN"), cellular network (e.g., 3G, 4G, 4G LTE, 5G, etc.), or any combination of these.

One of the two depicted user devices 106 is used by a patient 108 undergoing evaluation or monitoring for a behavioral health disorder and has a microphone 107 to allow the user to record voice inputs. The user device 106 executes client software to that prompts the user to record a voice input using the attached microphone 107 and interacts with the cloud server system 112 to provide the voice inputs for analysis. It may also allow the user to take a behavioral health assessment, such as a PHQ-9, GAD-7 (generalized anxiety disorder), or PCL-5 (PTSD Checklist), and provide the results to the cloud server system 112. Other suitable clinically validated self-report assessments in mental health for use with examples according to this disclosure include the Columbia Suicide Severity Rating Scale ("C-SSRS"), Altman Self-Rating Mania Scale ("ASRM"), Panic Disorder Severity Scale ("PDSS"), Fear Questionnaire ("FQ"), Social Phobia Inventory ("SPIN"), Liebowitz Social Anxiety Scale Self Report ("LSAS-SR"), Brief Addiction Monitor ("BAM"), DSM-5 Checklist for Substance Use Disorder, NIH Patient Reported Outcomes Measurement Information System ("PROMIS") (including PROMIS-Social Isolation, PROMIS-Stigma, PROMIS-General Self Efficacy, and PROMIS-Participate in Social Roles), and the Brief Revised Working Alliance Inventory ("BR-WAI"). The user device 106 also includes non-volatile storage (not shown) where it saves the recorded voice inputs or assessments before providing them to the cloud server system 112. The client software can also receive communications from behavioral health providers or the cloud server system 112, such as text or voice messages, as well as other information about their behavioral health symptomatology and progress.

The other depicted user device 102 is used by a behavioral health professional 104 to review behavioral health assessments generated by the cloud server system 112. The behavioral health professional 104 executes client software that interacts with the cloud server system 112 to obtain results of behavioral health assessments for patients that the behavioral health professional 104 is working with. The client device 102 also allows the behavioral health provider to communicate with the patient 108, such as to text message or have voice or video calls with the patient 108 or to suggest interventions to the patient 108.

The client devices 102, 106 may be any suitable client device for the respective user, including handheld devices (such as smartphones and tablets), portable devices (such as laptop computers), or desktop computers. In some examples the client devices 102, 106 may execute client software via a web browser by accessing a link (e.g., a uniform resource locator or "URL") to a web application hosted by the cloud server system 112. In other examples, the client software for one or both client device 102, 106 may be locally executed. And while this example system 100 shows only two client devices 102, 106, any number of client devices may be included in example systems according to this disclosure. Further, it should be appreciated that the client devices 102, 106 may be remote from each other. For example, the patient 108 may have their client device 106 at their home, while the behavioral health professional 104 may have their client device 102 at their office.

The cloud server system 112 includes one or more server computers located remotely from the client deices 102, 106. The cloud server system 112 executes software to analyze received behavioral health assessments and voice inputs from patients and provide an assessment of their behavioral health. To do this, the cloud server system 112 maintains one or more ML models that have been trained to analyze voice inputs and baseline data and generate corresponding predictions regarding changes in the patient's behavioral health from the baseline. As will be discussed in more detail below, an ML model may be trained to determine a composite assessment score or quantify a deviation from the baseline based on a voice input.

For example, an ML model may be trained to generate a composite PHQ-9 score based on a voice input from a patient and the patient's baseline data to generate a predicted change. However, some ML models may be trained to determine only a change for only one score, or a subset of scores, for one or more portions of an assessment that may then be used to determine a predicted change in composite score for the entire assessment. For example, nine separate ML models may be trained to generate a predicted change for a specific question in the PHQ-9. A composite change may then be generated by adding the predicted changes from each of the nine ML models. Further, some examples may determine information about subfactors based on a patient's voice input and baseline data. The results of the ML model's analysis may be stored in a data store at the cloud computing system 112 and may be accessed by any behavioral health professional with appropriate permission.

Figure 2:
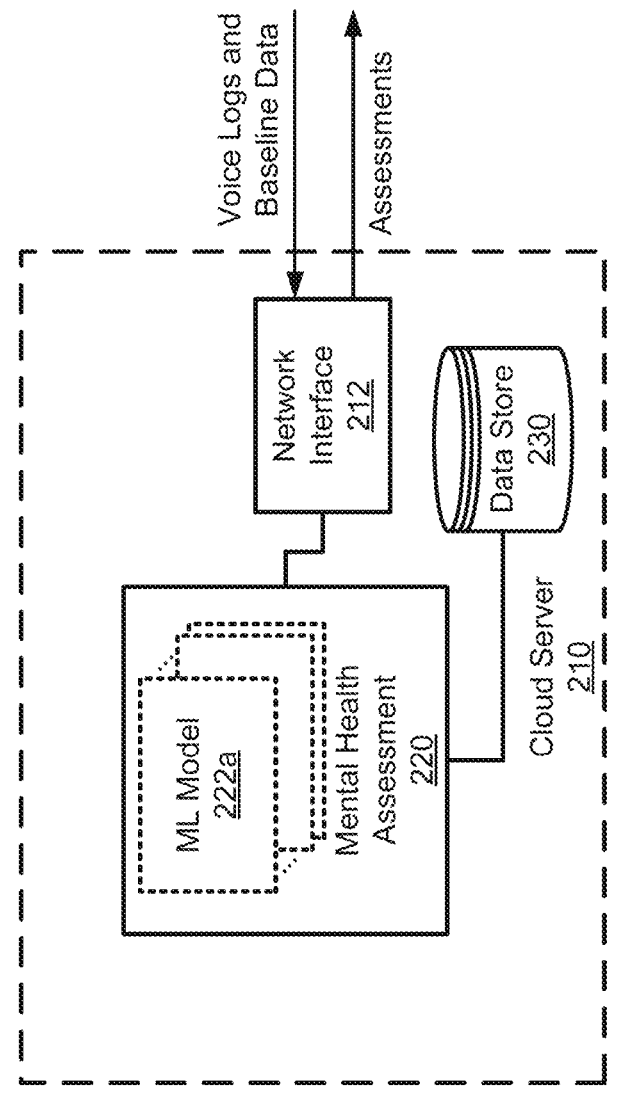
FIG. 2 shows an example cloud server for predicting clinically meaningful changes in behavioral health symptomatology using patient voice inputs.

Referring now to FIG. 2, FIG. 2 shows an example cloud server 210 suitable for use with various example systems and methods for predicting CMC in behavioral health symptomatology using voice inputs. The cloud server 210 includes behavioral health assessment software 220 that receives patient inputs and baseline behavioral samples from remote computing devices via its network interface 212. As discussed above, the patient inputs and baseline behavioral samples may be received from patients' client devices directly. Though in some examples, patient inputs may first be sent to a behavioral health professional or a behavioral health provider that may aggregate multiple patient inputs from various patients and transmit the patient inputs to the cloud server 210 for processing. Further, in some examples, the patient may take an assessment, such as the PHQ-9, and record an input, such as a voice or video recording, as a part of a session with a behavioral health professional, which information may be provided to the cloud server 210. Baseline patient inputs and assessments may be stored in the datastore 230 as baseline behavioral samples for use in analysis of subsequent patient inputs. When a supplemental patient input is received from a patient, it may be immediately inputted into a corresponding ML model 220a-n along with the corresponding baseline behavioral sample by the behavioral health assessment software or it may be stored in the data store 230 for later processing.

While some examples may capture a single baseline behavioral sample for a patient, some examples may capture multiple candidate baseline behavioral samples for a patient. Different baseline behavioral samples may be captured based on different criteria, such as time of day (e.g., a baseline morning behavioral sample and a baseline evening behavioral sample), time of year (e.g., spring, summer, etc.), menstrual cycle, weekday or weekend, vacation, or any other suitable event or environmental condition of interest. Supplemental behavioral samples may then be analyzed with respect to a suitable corresponding baseline behavioral sample to assess whether the patient's behavioral symptomatology has changed in a clinically meaningful way based on that particular criterion. Such a correspondence may be determined based on explicit information provided by the patient, such as by asking the user about biological cycles, obtaining time information (e.g., a time stamp) for the supplemental behavioral sample, or by obtaining publicly available information, such as the date and time, the patient's location, etc.

The behavioral health assessment software 220 includes one or more ML models 222a-n that are trained to provide behavioral health assessments based on patient inputs and baseline behavioral samples. The ML models 222a-n may all be trained to perform the same assessment or different ML models may be available to perform different types of behavioral health assessments. For example, one ML model 220a may be trained to generate a predicted change in composite PHQ-9 score based on a patient input, while ML models 220b-j may each be trained to generate a predicted change in a score for a different PHQ-9 question. Further, another ML model may be trained to generate a predicted change in composite score for the GAD-7 assessment based on a patient input and corresponding baseline behavioral sample, while further ML models may be trained to generate predicted changes in scores for individual questions on the GAD-7 assessment. In addition, the cloud server 210 may have multiple ML models trained to perform the same assessment, such as to process multiple voice inputs in parallel.

As discussed above, a patient may have multiple different baseline behavioral samples corresponding to different conditions, environmental factors, or biological cycles. Thus, the behavioral health assessment software 220 may need to select a particular baseline behavioral sample to use to perform its analysis. The different baseline behavioral samples correspond to different detectable recurring events, such as those discussed above. A baseline behavioral sample may then be selected based on a categorization of the subsequent behavioral sample, metadata associated with the subsequent behavioral sample (e.g., time stamp, location stamp, contextual information, etc.), a digital profile of the individual that may include patient-provided information, third-party systems, including social media information, or other public information. In some cases, baseline behavioral samples may be associated with specific time stamps relative to a particular biological cycle, such as a menstrual cycle, sleep cycle, eating cycle, seasonal changes in the patient's body, etc. In addition, a received supplemental behavioral sample may also have a time stamp, which may be used to select a corresponding baseline behavioral sample that carries a similar time stamp relative to a particular biological cycle.

Rather than predicting changes in scores of specific questions or for a full assessment, some examples may employ trained ML models to determine predicted changes in scores for subfactors corresponding to groups of questions on a written assessment. For example, subfactors corresponding to the following groups of symptoms may be used: (1) affective subfactor: anhedonia and depressed mood (corresponding to questions 1-2 on the PHQ-9), (2) internalizing subfactor: worth or guilt and suicidality (corresponding to questions 6 and 9 on the PHQ-9), (3) sensorimotor subfactor: concentration and psychomotor issues (corresponding to questions 7-8 on the PHQ-9), and (4) somatic subfactor: sleep, fatigue, and appetite (corresponding to questions 3-5 on the PHQ-9). Thus, the subfactors may be correlated with scores for one or more questions on a PHQ-9 assessment and may be of more clinical value than changes in scores of specific questions or for the entire PHQ-9. For example, a patient's PHQ-9 score may appear to remain essentially the same, but answers to different questions within the assessment may change significantly. Thus, analyzing changes in individual questions or subfactor, which are groupings of individual questions, may provide more granular information about the patient's behavioral health assessment. Consequently, the behavioral health assessment software 220 may have any number or types of ML models, such as those discussed above, depending on the configuration of the cloud server 210.

While FIG. 2 only depicts a single cloud server 210, it should be appreciated that a cloud server system may include multiple cloud servers 210. Further, such cloud servers may be configured with different types of ML models to assess different types of behavioral health disorders. Thus, a single cloud server system 112 may be able to allocate voice inputs related to different behavioral health assessments to corresponding cloud servers 210 for analysis.

After processing a patient input and corresponding baseline behavioral samples using the behavioral health assessment software 220, it generates a predicted change in behavioral health symptomatology based on the baseline behavioral sample that may then be communicated to a behavioral health provider, such as discussed above with respect to FIG. 1. If the predicted change indicates a clinically significant change, a corresponding indication may be provided as well. The assessments may also be stored in a data store 230 where they may later be retrieved as needed by a behavioral health professional or a patient.

Figure 3:
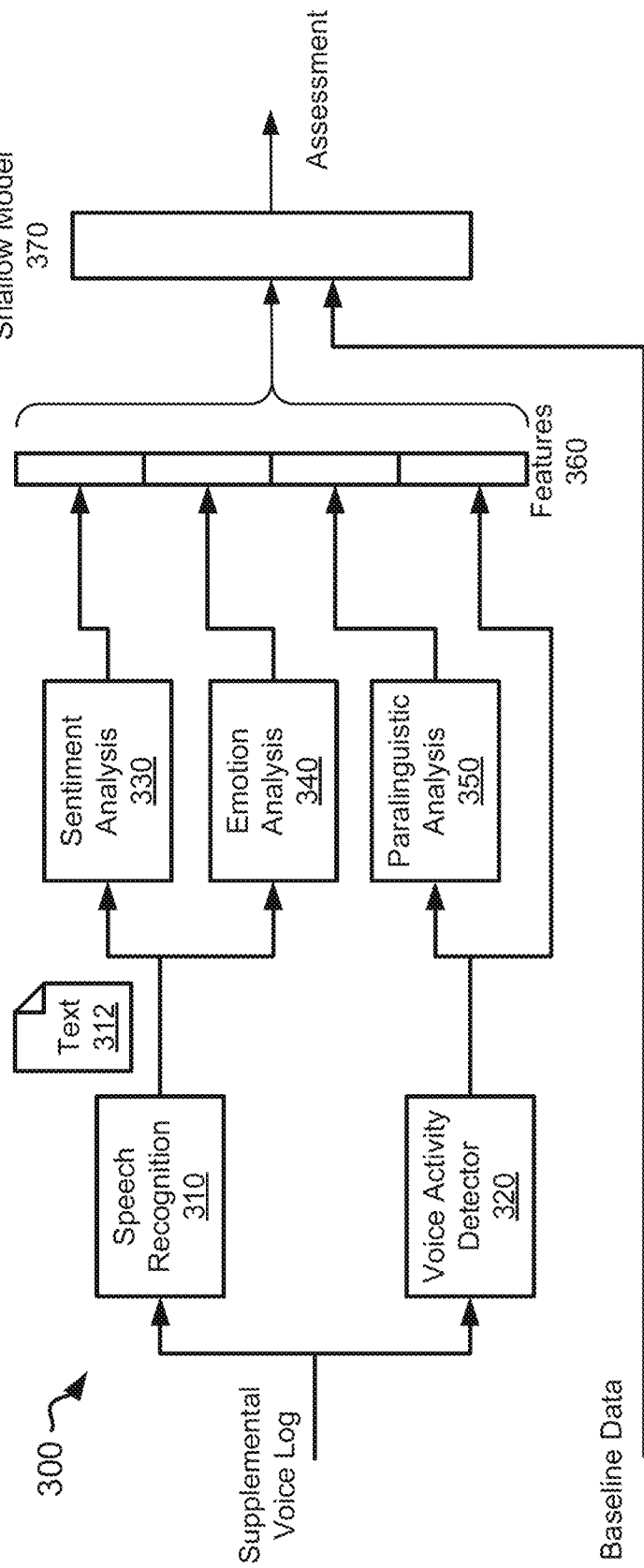
FIG. 3 shows an example system for predicting clinically meaningful changes in behavioral health symptomatology using patient voice inputs.

Referring now to FIG. 3, FIG. 3 shows example behavioral health assessment software 300 suitable for use with systems and methods for predicting CMC in behavioral health symptomatology using patient inputs, such as described above with respect to FIGS. 1 and 2. The behavioral health assessment software 300 includes a speech recognition component 310 and a voice activity detector 312 which accept input audio signals from a voice input. The output of the speech recognition component 310 is provided to a sentiment analysis component 330 and to an emotion analysis component 340, each of which processes the recognized speech to generate sentiment and emotion feature information that will be provided to a trained ML model 370 for analysis. In addition, the voice activity detector 320 identifies when audio within the input voice input includes speech audio and provides the corresponding speech audio to a paralinguistic analysis component 350. In addition, the voice activity detector 320 provides voice activity information as a feature for input into the trained ML model 370.

The features 360 provide input information for the trained ML model 370. As discussed above, the information generated by the sentiment analysis component 330, the emotion analysis component 340, and the paralinguistic analysis component 350, as well as the output from the voice activity detector are aggregated as input features 360 for the ML model 370 along with the baseline voice input and assessment score, e.g., a PHQ-9 score.

As mentioned above, the speech recognition component 310 may employ any suitable speech recognition technique to generate a text transcript of the input speech. The sentiment analysis component 330 employs a natural language processor to perform sentiment analysis, which may include detecting topic shifting, verbosity, sentence and discourse structure. In some examples, the sentiment analysis component 330 may be specially trained according to the specific behavioral health disorder or symptomatology to be analyzed, such as depression, anxiety, or PTSD. Similarly, the emotion analysis component 340 includes a trained natural language processor, however, this NLP detects apparent emotion, e.g., mood, energy, intensity, in the speech information. As with the sentiment analysis component 330, the emotion analysis component 340 may be specially trained according to the specific behavioral health disorder or symptomatology to be analyzed.

The paralinguistic analysis component 350 may be any suitable paralinguistic analysis technique. For example, such a suitable technique may be as described in "Improving Speech Representations and Personalized Models Using Self-Supervision" to Shor et al or "Universal Paralinguistic Speech Representations Using Self-Supervised Conformers" to Shor et al.

After the various features 360 have been generated by the corresponding components of the software 300, the baseline voice input is also processed to generate features as inputs to the ML model 370. The sets of features and the baseline PHQ-9 score are provided to the ML model 370 for analysis. In this example, the ML model 370 is a shallow learning model trained to determine changes between an input feature set and a baseline feature set. Any suitable shallow model may be used; however, different embodiments may employ other types of models, including deep-learning models.

The output of the model may be a numerical value representing the difference between the voice input and the baseline data. For example, the output may be a value indicating a predicted change in an assessment score, e.g., a score on the PHQ-9 test. If the user's baseline PHQ-9 score was 15, the output may be +4.7, indicating that the user's condition has worsened to a predicted score of approximately 20, or −3.2, indicating that the user's condition has improved to a predicted score of approximately 12.

In some examples, the behavioral health assessment software 220 may generate a vector of values that indicate predicted changes in individual scores for questions in the assessment or for predicted changes in scores for subfactors corresponding to questions in the assessment. For example, for an embodiment that includes nine discrete ML models, each corresponding to one of the questions on the PHQ-9 assessment, the output from each of the models may be aggregated into a vector of nine values, one for each of the nine questions on the assessment. In another example that employs four discrete ML models, one for each of the subfactors discussed above, the behavioral health assessment software 220 may output a vector of four values, one for each of the four subfactors. For other types of assessments, such as anxiety or PTSD, the outputs may correspond to the specifics of those assessments, such as the number of questions or corresponding subfactors.

After obtaining the output from the ML model(s) for a particular voice input, the behavioral health assessment software 220 may determine whether one or more thresholds has been satisfied by the output. For example, if the predicted output is a predicted change in a composite assessment score, the behavioral health assessment software 220 may compare the predicted change against a first threshold value corresponding to a small, but significant change in the assessment score, and a second threshold value corresponding to a larger change in the assessment score. For example, for the PHQ-9 score, the first threshold may be a value of five, which may indicate a CMC in the assessment score, while the second threshold may be nine, indicating a significant worsening of the patient's depression.

Similarly, in examples that generate vectors of values, thresholds may be established for each vector value. In an example that generates a vector of scores corresponding to subfactors for the PHQ-9 assessment, one subfactor may correspond to a group of three PHQ-9 questions and thus has a range from zero to nine, i.e., three times the score range for each question, which is zero to three. Thus, a first threshold for the subfactor may be three, while a second threshold may be five. A similar approach may be used to establish thresholds for individual assessment questions, such as a first threshold of one and a second threshold of two or three.

Based on which threshold or thresholds are satisfied, the behavioral health assessment software may identify a corresponding intervention. For example, a change that satisfies only the first threshold for a composite assessment score may generate a recommendation for the patient to re-take the PHQ-9, while a change that satisfies both the first and second thresholds may generate a recommendation for the patient's behavioral health professional to contact the patient to discuss any issues the patient may be having. The use of multiple thresholds may enable the system to cast a wide net to identify patients who may be decompensating in some fashion, while avoiding false negatives. It may also use the higher threshold to avoid potential false positives for more intensive interventions.

The recommendations, as well as the predicted changes, may be provided to a behavioral health professional or to the patient depending on the predicted changes. For example, if a patient's score satisfies the first threshold, but not the second threshold, the behavioral health assessment software 220 may transmit a message to the patient requesting that they take the PHQ-9 assessment. To do so, the patient may click a link in the message to take the PHQ-9 assessment via an online form provided by the cloud server 210. The patient's assessment may then be stored in the data store 230. It may also be compared against the patient's baseline PHQ-9 score and, if the difference satisfies the second threshold, the behavioral health assessment software 220 may notify the patient's behavioral health professional. However, if the predicted change from the voice input analysis satisfies the second threshold, a message may be provided to the patient's behavioral health professional indicating a recommended intervention, such as contacting the patient about their behavioral health disorders.

Similarly, thresholds may be used to detect improvement in a patient's symptoms, which may be used to trigger interventions, such as positive feedback from a behavioral health professional. For example, a third threshold may be established at a level indicating a CMC improvement, e.g., a minimally clinically important different ("MCID") such as a predictive change of negative five. If the score satisfies the third threshold, the behavioral health professional may be notified and a recommended intervention, such as a positive message to the patient, may be provided to them.

Using such a system, patients can provide voice inputs for analysis of potential changes in the progression of their behavioral health without repeatedly re-taking a written assessment. In addition, behavioral health professionals can more effectively monitor their patients and devote more time to patients experiencing more severe decompensation, while still keeping track of other patients who may be holding steady or improving.

However, because patients may be monitored over an extended period of time, a patient's baseline data may become less accurate or meaningful over time. When the baseline data is sufficiently outdated, the patient may be prompted to provide a new set of baseline data, such as by re-taking an assessment and providing a corresponding voice input.

To determine when the baseline data is outdated, the behavioral health assessment software 220 may determine an elapsed amount of time since the baseline data was initially acquired. If the elapsed time satisfies a threshold, the baseline data may be deemed outdated and a new baseline may be requested from the patient. In some examples, the ML model 370 may output a score, as discussed above, but also a confidence score, such as a real number between zero and one. If the confidence score for a subsequent assessment reaches a threshold, e.g., the confidence score drops below 85%, the behavioral health assessment software 220 may request the patient submit new baseline data.

In some examples, new baseline behavioral samples may be obtained at a particular cadence or schedule. For example, a new baseline behavioral sample may be captured based on a particular biological cycle, such as the beginning or end of such a cycle. Such new baseline behavioral samples may replace any existing baseline behavioral samples or the new baseline behavioral sample may only replace a corresponding baseline behavioral sample. For example, if a patient has baseline behavioral samples corresponding to a menstrual cycle, a sleep cycle, and one each for weekdays and weekends, a new baseline behavioral sample corresponding to a weekend may only replace the prior weekend baseline behavioral sample without affecting the other baseline behavioral samples.

In some examples, a new baseline behavioral sample may be requested based on detected changes in the patient's environment. For example, location data may be obtained along with behavioral samples. If location data for a supplemental behavioral sample differs significantly from the baseline behavioral sample, a new baseline behavioral sample may be obtained. Similarly, other detected environmental changes at the patient's location may cause a new baseline behavioral sample to be requested, including changes in social network information, changes in weather or geopolitical events, seasonal changes, detected hazardous events, etc.

Figure 4A:
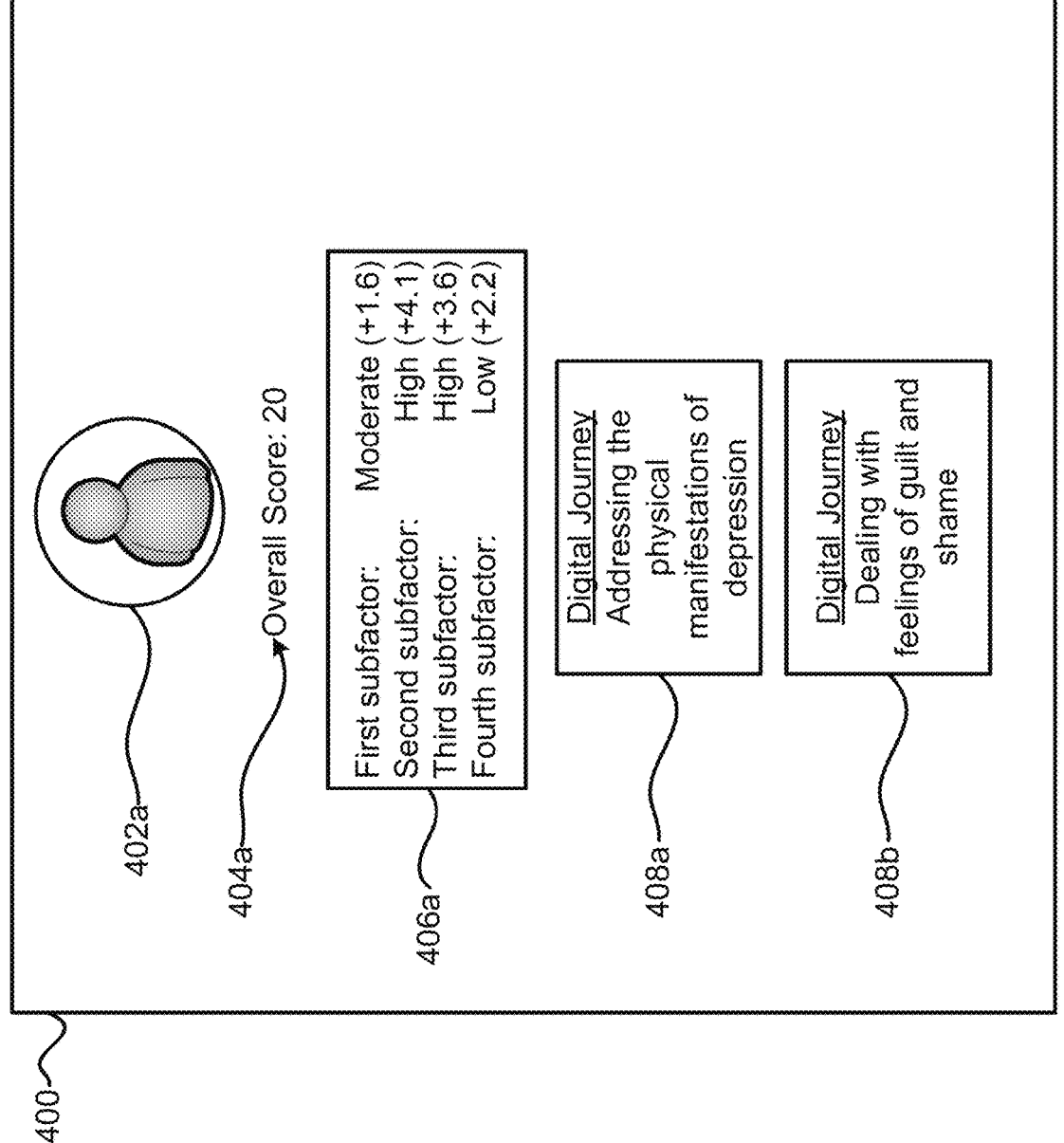
FIGS. 4A-4B show example graphical user interfaces for software for predicting clinically meaningful changes in behavioral health symptomatology using patient voice inputs.
Figure 4B:
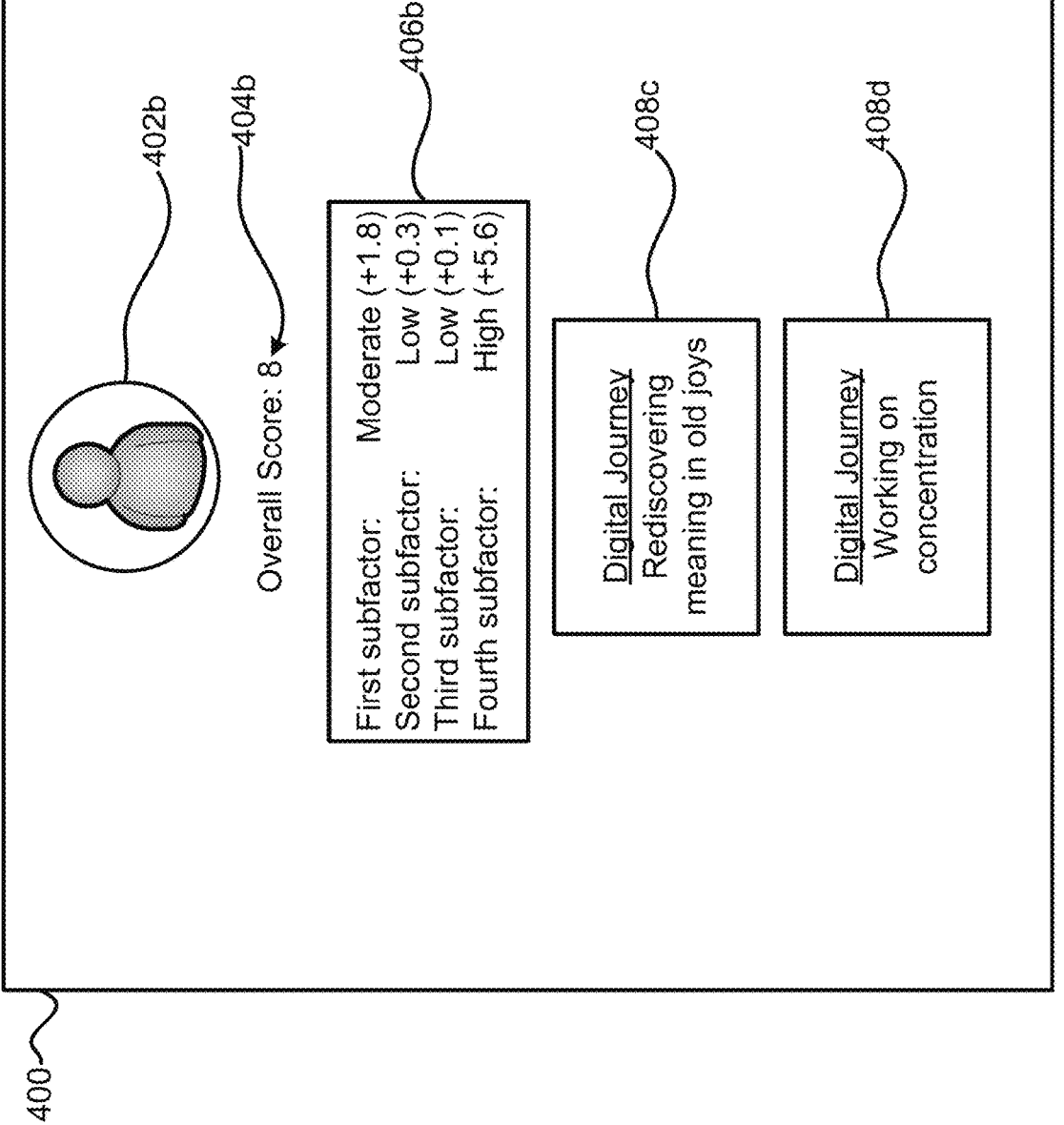

Referring now to FIGS. 4A-4B, FIG. 4A shows an example graphical user interface ("GUI") 400 that may be provided to a behavioral health professional 104 at their client device 102. In this example, the behavioral health professional 104 accesses the cloud server system 112 using a web browser, which allows them to navigate to different patients' assessment information, which is presented using the GUI 400.

In this example, the GUI 400 provides a representation 402a of the patient, such as a photograph of the patient 108 or the patient's name, a current behavioral health assessment score 404a, such as their most recent PHQ-9 score. The GUI 400 also provides more granular information about the patient's behavioral health, such as qualitative and quantitative predicted changes 406a for the subfactors identified for their behavioral health assessment. These provide the behavioral health professional 104 a way to quickly understand the patient's current behavioral health symptomatology and any improvement or decompensation. In this example, because the patient's second and third subfactor scores have worsened significantly, the behavioral health assessment software 220 has provided suggested interventions 408a-b for the patient 108. The behavioral health professional 104 can then decide how to interact with the patient 108, such as by initiating contact with the patient 108 through a voice or video call or using text messaging. The behavioral health professional 104 can also select one or more of the suggested interventions 408a-b, or other available interventions, and provide a notification to the patient 108 to review the content, such as one or both of the interactive content items suggested by the behavioral health assessment software 220.

FIG. 4B shows the example GUI 400 in the context of another patient's assessment. As with the example discussed above with respect to FIG. 4A, the GUI 400 provides a representation 402b of the patient and their most recent behavioral health assessment score 404b. In addition, their predicted subfactor score changes are provided along with suggested interventions 408c-d, which in this case are different from those suggested in FIG. 4A due to the patient's different behavioral health assessment.

Figure 5:
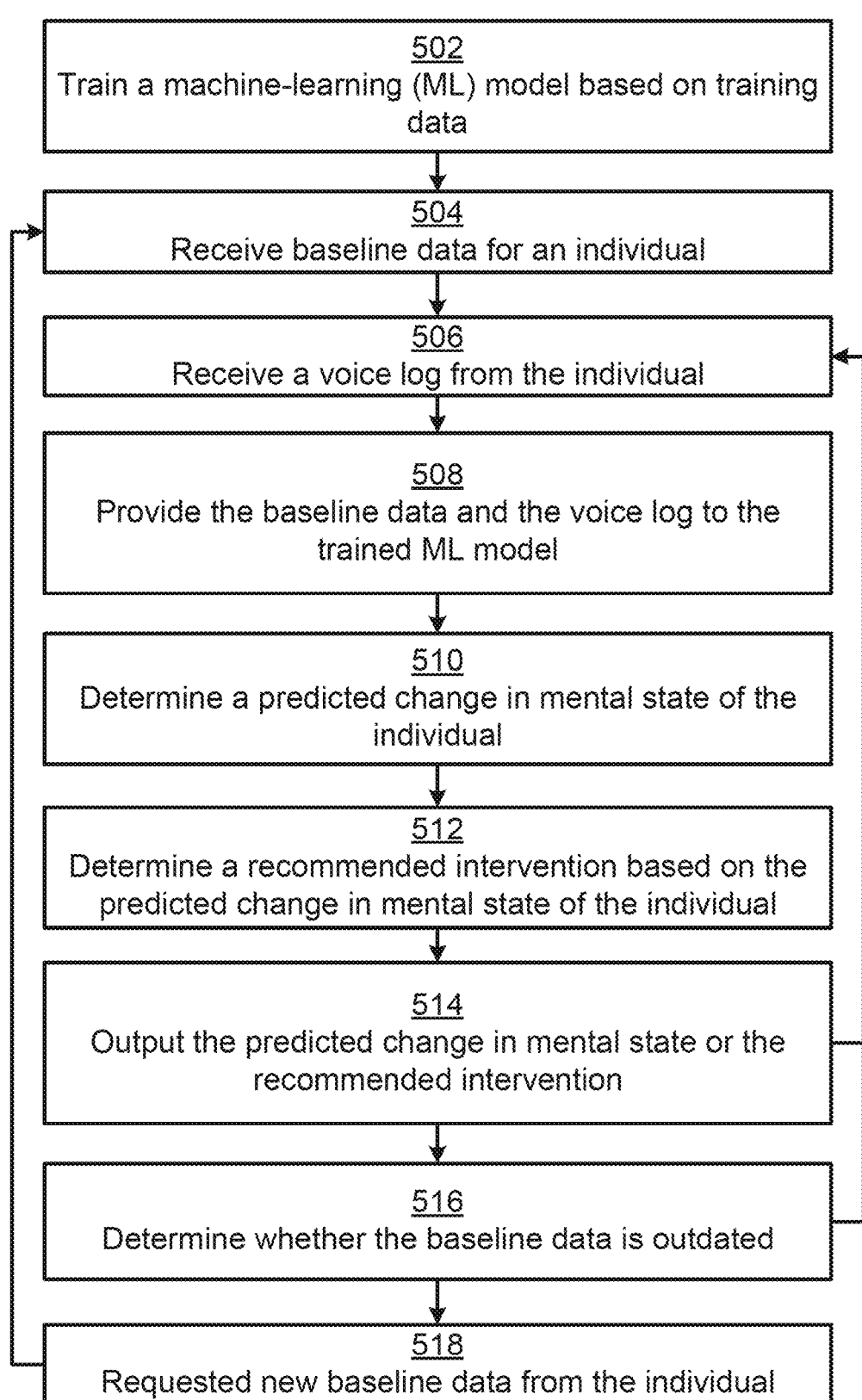
FIG. 5 shows an example method for predicting clinically meaningful changes in behavioral health symptomatology using patient voice inputs.

Referring now to FIG. 5, FIG. 5 shows an example method 500 for predicting CMC in behavioral health symptomatology using voice inputs. The example method 500 will be discussed with respect to the system 100 shown in FIG. 1, the cloud server 210 shown in FIG. 2, and the system 300 shown in FIG. 3; however, it should be appreciated that example methods according to this disclosure may be performed by any suitable system for predicting CMC in behavioral health symptomatology using voice inputs.

At block 502 one or more ML models are trained to predict changes in a behavioral health assessment from baseline data and patient voice inputs. In this example, the ML model(s) are trained using a self-supervised training method; however, any suitable training method may be used, whether supervised, unsupervised, or semi-supervised. As discussed above with respect to FIGS. 1-3, a system may employ multiple ML models to predict CMC in behavioral health symptomatology. The different ML models may be trained based on different behavioral health assessments, e.g., PHQ-9, GAD-7, or PCL-5, or different ML models may be trained to predict changes in scores for individual questions on such assessments or subfactors associated with one or more questions on such assessments. Some examples may be trained to predict assessment scores based on the baseline behavioral samples and patient inputs rather than a change from the baseline assessment score from the baseline behavioral sample. Further, different combinations of such ML models may be trained based on the requirements for a particular system.

In some example, one or more ML models may be trained to also output a confidence score. For example, an ML model may be trained to determine a change in behavioral health symptomatology based on a PHQ-9 assessment and to output a confidence value, e.g., real number from 0 to 1, associated with the determined change. The confidence value may indicate the quality of the predicted change. For example, a score of 0.92 may indicate a confidence of 92% in the accuracy of the predicted change. Such information may be used to determine if baseline data is outdated as will be discussed in more detail below.

At block 504, the cloud server 210 receives a baseline behavioral sample indicating an initial behavioral health symptomatology of an individual, such as a patient. The baseline behavioral sample in this example includes a behavioral health assessment score and a voice input captured contemporaneously with the individual taking the behavioral health assessment that provided the score. Thus, the voice input and the behavioral health assessment score both represent the individual's behavioral health symptomatology at approximately the same time. The baseline behavioral sample may be stored in the data store 230 or may be provided to the cloud server 210 by a behavioral health professional 104 after conducting the assessment with the individual 108 and obtaining a voice input.

In some examples, the baseline behavioral sample may be obtained from the individual by receiving it from the individual's client device 106. For example, the user may take the assessment via a web site provided by the cloud server system 112 and record a voice input via the same web site, which may allow the assessment score and voice input to be stored at the cloud server 210. Alternately, the individual may take the assessment and record the voice input at their client device 106 and transfer the assessment score and the voice input to the cloud server 210.

In some examples, as discussed above, the cloud server system 112 may receive multiple baseline behavioral samples for a single patient. The different baseline behavioral samples may corresponding to different biological cycles or environmental conditions, such as menstruation, sleep, weather, date or time, or season.

After receiving the baseline behavioral sample, the cloud server 210 associates the assessment score and the patient input to each other and designates them as a baseline behavioral sample for the patient. For example, the cloud server 210 may associate the baseline behavioral sample with a profile for the individual 108.

At block 506, the cloud server 210 receives a supplemental behavioral sample including a supplemental patient input, such as a voice recording, from the individual. As discussed above, a patient may provide additional patient inputs over time to allow the cloud server system 112. To provide the supplemental data, the individual 108 may access a web site provided by the cloud server system 112 and record the patient input using their client device's microphone 107. The patient input may be recorded directly by the cloud server 210 and then stored in its data store 230. It may also be associated with the individual's profile. Alternatively, the individual may record the patient input at their own client device 106 before uploading it to the cloud server system 112. Similarly, the individual 108 may record the patient input during an appointment with a behavioral health professional, which may then provide the voice input to the cloud server system 112.

Supplemental behavioral samples may be provided on a regular periodic basis, such as daily, once per week, twice per month, or at any other interval recommended to the individual. In some examples, the supplemental behavioral sample may be provided at any time when the individual 108 decides to provide a voice input.

Supplemental behavioral sample may include other information, such as a date and time the patient input was captured. For example, if the voice input was captured at the individual's client device 106, it may not be uploaded to the cloud server system 112 immediately. Thus, capturing the date and time the log was recorded may assist with monitoring the patient's behavioral health. In addition, other information may be captured and provided as supplemental data, such as another assessment score, information about any biological cycles or any environmental information.

At block 508, the cloud server 210 provides the baseline behavioral sample and the supplemental behavioral sample to the one or more trained ML models to predict a change in behavioral health symptomatology. As discussed above with respect to block 502, the trained ML models were trained to output an indication of a predicted change in behavioral health symptomatology based on the received input data.

At block 510, the ML model(s) determine a predicted change in behavioral health symptomatology of the individual. For example, if the cloud server 210 employs a single ML model trained to determine a predicted change in PHQ-9 score from the baseline data, the ML model may output a number indicating a predicted change in the patient's PHQ-9 score, e.g., value between −27 and +27. In some examples, the cloud server 210 may employ multiple ML models, each trained to predict a change in a particular question of an assessment. In an example configured to predict a change in a GAD-7 assessment that employs seven trained ML models, each of the trained ML models may output a predicted score between −3 and +3, representing the maximum changes for a score on a single question. The cloud server may then obtain seven different predicted scores corresponding to the seven questions on the GAD-7 assessment. Alternatively, as discussed above, some examples may employ ML models trained to predict changes in subfactors, such as those discussed above with respect to FIG. 2. Thus, each of the trained ML models may output a value within a range corresponding to the maximum changes for the particular subfactor.

Some examples may output predicted assessment scores, question scores, or subfactor scores rather than predicted changes. The change in behavioral health symptomatology may then be assessed based on the differences between the predicted score(s) and the score(s) from the baseline data.

At block 512, the cloud server system 112 determines a recommended intervention based on the predicted change in behavioral health symptomatology. The cloud server system 112 may maintain information associating different predicted changes in behavioral health symptomatologies with recommended interventions. For example, as shown in FIGS. 4A-4B, a predicted change in the second and third subfactors for an assessment may be associated with different digital interventions, which may be videos, worksheets, articles, or interactive digital exercises. The various interventions and associations with different types of changes may be stored in one or more data stores accessible by the cloud server system 112. The cloud server system 112 may thus access the corresponding data store(s) to determine which assessment(s) to recommend to the behavioral health provider 104 or to the individual 108 based on the predicted changes in behavioral health symptomatology.

At block 514, the cloud server 210 may output the predicted change in behavioral health symptomatology. For example, after determining the predicted change in behavioral health symptomatology, the cloud server 210 may store the predicted change in its data store 230 or it may provide it to a behavioral health professional 104 or to the individual 108. It may do so by providing the predicted change via a web page provided by the cloud server 210 or cloud server system 112. It may also transmit a notification, such as an email, text message, or in-client-software message to the behavioral health provider 104 or the individual 108. The method 500 may then return to block 506 when it receives another voice input from the individual or it may determine whether the baseline data is outdated or not at block 516.

At block 516, the cloud server 210 determines whether the baseline behavioral sample is outdated. In this example, the cloud server 210 is configured to determine that baseline behavioral sample is outdated four weeks after it was initially obtained, such as based on a time or date stamp associated with the baseline behavioral sample. In some examples, the cloud server may determine that the baseline behavioral sample is outdated based on confidence scores output by one or more ML models based on supplemental data. For example, as discussed above with respect to block 502, ML models may be trained to output confidence scores associated with the outputted predicted changes in behavioral health symptomatology. In one example, if a confidence score output by a trained ML model is below a threshold, e.g., below 90%, the cloud server 210 may determine that the baseline behavioral sample is outdated.

If multiple ML models are executed for a received supplemental behavioral sample, each providing a corresponding confidence score, the cloud server 210 may determine that the baseline behavioral sample is outdated if more than a threshold number of the outputted confidence scores are below the threshold. In some examples, the cloud server 210 may determine the baseline behavioral sample is outdated if two or more successive patient inputs result in confidence scores below a threshold. Thus, a single occurrence of a confidence score below a threshold may be insufficient to determine baseline data is outdated, but continued low confidence scores may result in the determination that the baseline behavioral sample is outdated.

In some examples, as discussed above, a baseline behavioral sample may be outdated at a regular schedule based on a biological cycle or environmental condition, such as at the beginning of a biological cycle or a change in an environmental condition, such as a change in location, weather, season, etc. Further, if multiple baseline behavioral samples are maintained for a single patient, each corresponding to a different biological cycle or environmental condition, the different baseline behavioral samples may be independently recalibrated based on different conditions.

If the baseline behavioral sample is not determined to be outdated, the method 500 returns to block 506. Otherwise, it proceeds to block 518.

At block 518, the cloud server 210 transmits a request to the individual to provide new baseline behavioral sample and the method 500 returns to block 504 where new a baseline behavioral sample is received.

Figure 6:
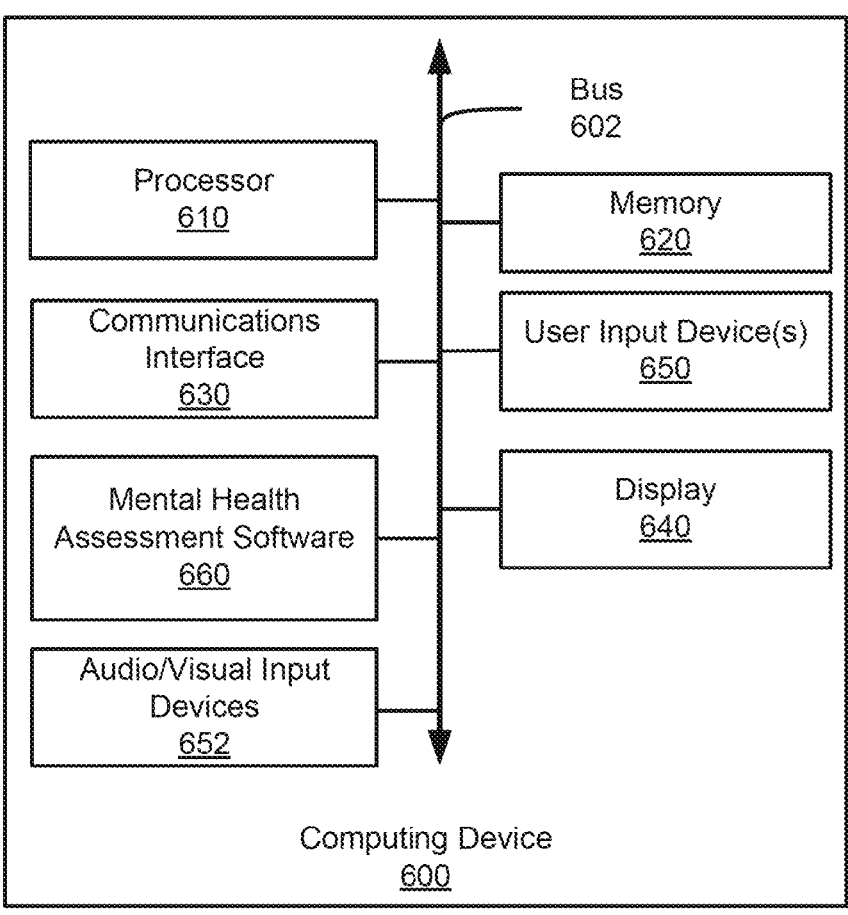
FIG. 6 shows an example computing device suitable for use with systems and methods for predicting clinically meaningful changes in behavioral health symptomatology using patient voice inputs.

Referring now to FIG. 6, FIG. 6 shows an example computing device 600 suitable for use in example systems or methods for predicting CMC in behavioral health symptomatology using voice inputs according to this disclosure. The example computing device 600 includes a processor 610 which is in communication with the memory 620 and other components of the computing device 600 using one or more communications buses 602. The processor 610 is configured to execute processor-executable instructions stored in the memory 620 to perform one or more methods for predicting CMC in behavioral health symptomatology using voice inputs according to different examples, such as part or all of the example method 500 described above with respect to FIG. 5. The computing device 600, in this example, also includes one or more user input devices 650, such as a keyboard, mouse, touchscreen, microphone, etc., to accept user input. The computing device 600 also includes a display 640 to provide visual output to a user.

The computing device 600 also includes a communications interface 640. In some examples, the communications interface 630 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods according to this disclosure. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example one or more non-transitory computer-readable media, that may store processor-executable instructions that, when executed by the processor, can cause the processor to perform methods according to this disclosure as carried out, or assisted, by a processor. Examples of non-transitory computer-readable medium may include, but are not limited to, an electronic, optical, magnetic, or other storage device capable of providing a processor, such as the processor in a web server, with processor-executable instructions. Other examples of non-transitory computer-readable media include, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code to carry out methods (or parts of methods) according to this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
receiving a baseline behavioral sample indicating an initial behavioral health symptomatology of an individual, the baseline behavioral sample comprising (i) an audio recording, (ii) a video recording, or (iii) a multimedia recording, and the initial behavioral health symptomatology indicative of a behavioral health disorder;
receiving a subsequent behavioral sample including a supplemental voice recording from the individual, the supplemental voice recording received after the baseline behavioral sample and comprising the same or different content as the baseline behavioral sample;
computing a difference score from a trained machine-learning ("ML") model by providing the baseline behavioral sample and the subsequent behavioral sample as input to the trained ML model, wherein the difference score indicates a predicted change in behavioral health symptomatology of the individual based on determined changes between the baseline behavioral sample and the subsequent behavioral sample, the trained ML model being configured to output a score indicating a predicted change in behavioral health symptomatology based on input data;
outputting the predicted change in behavioral health symptomatology to a client device executing a graphical user interface indicating the predicted change for an entity treating the individual;
determining whether the predicted change in behavioral health symptomatology satisfies a first threshold of a plurality of thresholds; and
in response to determining that the predicted change in behavioral health symptomatology satisfies the first threshold, provide a notification to the individual to perform a first intervention.

2. The method of claim 1, wherein:
the baseline behavioral sample comprises a baseline voice recording and a baseline assessment score, wherein the baseline assessment score is derived from a clinically validated assessment in behavioral health; and
the predicted change in behavioral health symptomatology indicates a predicted change in behavioral health symptomatology from the baseline assessment score in accordance with the clinically validated assessment.

3. The method of claim 2, wherein the clinically validated assessment includes multiple questions, each question capable of generating an independent score based on a self-reported answer wherein the trained ML model comprises a plurality of trained ML models, each trained ML model is trained to assess a predicted change in a subset composite score of a subset of questions on a clinical assessment test used to generate the baseline assessment score, and further comprising:
providing the baseline behavioral sample and the subsequent behavioral sample as input to each trained ML model of the plurality of trained ML models; and
outputting, for each trained ML model of the plurality of trained ML models, the predicted change in a subset composite score of the respective subset of questions on the assessment.

4. The method of claim 1, further comprising:
determining that the baseline behavioral sample requires recalibration based on an environmental condition or a completion of a corresponding biological cycle; and
in response to determining that the baseline behavioral sample requires recalibration, generating a request to update the baseline behavioral sample at a digital device of the individual.

5. The method of claim 1, wherein receiving the baseline behavioral sample comprises receiving a plurality of baseline behavioral samples, each baseline behavioral sample corresponding to a point in time along a biological cycle; and wherein computing the difference score includes:
selecting a target baseline behavioral sample among the plurality of baseline behavioral samples based on a timestamp of the subsequent behavioral sample relative to the respective point in time along the biological cycle of the target baseline behavioral sample, and
providing the target baseline behavioral sample and the subsequent behavioral sample as input to the trained ML model.

6. The method of claim 1, further comprising generating the trained ML model by training a model using pairs of behavioral samples at two different time points of a population of individuals, wherein such population does not include the individual of claim 1, and wherein each pair of behavioral samples includes a pair of voice recordings and a pair of assessment scores of a clinically validated assessment respectively at the two different time points.

7. The method of claim 1, wherein the difference score and the predicted change in behavioral health symptomatology represent a personalized screening of the individual and wherein the trained ML model is trained without personal data of the individual.

8. A system comprising:
one or more processors; and
a non-transitory computer-readable medium comprising program code that is executable by the one or more processors to:
receive a behavioral sample from an individual;
determine, using a trained machine-learning ("ML") model, a predicted change in behavioral health symptomatology based on a baseline behavioral sample for the individual and the behavioral sample, the predicted change in behavioral health symptomatology based on a difference score computed by the trained ML model based on the baseline behavioral sample for the individual and the behavioral sample;
determine whether the predicted change in behavioral health symptomatology satisfies a first threshold of a plurality of thresholds; and
in response to determining that the predicted change in behavioral health symptomatology satisfies the first threshold, output the predicted change in behavioral health symptomatology to a client device executing a graphical user interface indicating the predicted change for an entity treating the individual.

9. The system of claim 8, wherein the baseline behavioral sample comprises a baseline voice recording and a baseline assessment score, wherein the baseline assessment score is derived from a clinically validated assessment in behavioral health, and wherein the predicted change in behavioral health symptomatology indicates a predicted change in behavioral health symptomatology from the baseline assessment score in accordance with a clinically validated assessment.

10. The system of claim 8, wherein the baseline behavioral sample comprises a baseline voice recording and a baseline assessment score, wherein the baseline assessment score is derived from a clinically validated assessment in behavioral health and the clinically validated assessment includes multiple questions, each question capable of generating an independent score based on a self-reported answer, wherein the trained ML model comprises a plurality of trained ML models, each trained ML model is trained to assess a predicted change in a subset composite score of a subset of questions on a clinical assessment test used to generate the baseline assessment score, and the non-transitory computer-readable medium further comprises program code that is executable by the one or more processors to:

provide the baseline behavioral sample and a subsequent behavioral sample as input to each trained ML model of the plurality of trained ML models; and output, for each trained ML model of the plurality of trained ML models, the predicted change in a subset composite score of the respective subset of questions on the assessment.

11. The system of claim 8, wherein receiving the baseline behavioral sample comprises receiving a plurality of baseline behavioral samples, each baseline behavioral sample corresponding to an enumerated environmental condition; and wherein the non-transitory computer-readable medium further comprises program code that is executable by the one or more processors to:

determine a match between contextual information associated with a subsequent behavioral sample and the enumerated environmental condition of a target baseline behavioral sample, and provide the target baseline behavioral sample and the subsequent behavioral sample as input to the trained ML model.

12. The system of claim 8, wherein the trained ML model is configured to determine the predicted change in behavioral health symptomatology by analyzing sentiment, emotion, paralinguistic parameters, or a combination thereof associated with speech in a voice recording.

13. The system of claim 12, wherein the non-transitory computer-readable medium further comprises program code that is executable by the one or more processors to perform speech recognition on the voice recording and providing the recognized speech to analyze sentiment or emotion.

14. The system of claim 10, wherein the non-transitory computer-readable medium further comprises program code that is executable by the one or more processors to:

determining a recommended intervention based on the predicted changes in the subset composite scores; and providing the recommended intervention to the entity treating the individual.

15. A non-transitory computer-readable medium comprising program code that is executable by one or more processors to:

receive a behavioral sample from an individual;

determine, using a trained machine-learning ("ML") model, a predicted change in behavioral health symptomatology based on a baseline behavioral sample for the individual and the behavioral sample, the predicted change in behavioral health symptomatology based on a difference score computed by the trained ML model based the baseline behavioral sample for the individual and the behavioral sample;

determine a recommended intervention based on the predicted change in behavioral health symptomatology; and output the recommended intervention to a client device executing a graphical user interface indicating the predicted change for an entity treating the individual.

16. The non-transitory computer-readable medium of claim 15, further comprising program code that is executable by the one or more processors to:

determine whether the predicted change in behavioral health symptomatology satisfies a first threshold of a plurality of thresholds; and in response to determining that the predicted change in behavioral health symptomatology satisfies the first threshold, provide a notification to the individual to perform a first intervention.

17. The non-transitory computer-readable medium of claim 16, wherein the first intervention comprises retaking an assessment.

18. The non-transitory computer-readable medium of claim 16, further comprising program code that is executable by the one or more processors to:

determine whether the predicted change in behavioral health symptomatology satisfies a second threshold of a plurality of thresholds, the second threshold greater than the first threshold; and in response to determining that the predicted change in behavioral health symptomatology satisfies the second threshold, provide a notification to the entity treating the individual of the predicted change in behavioral health symptomatology.

19. The non-transitory computer-readable medium of claim 18, further comprising program code that is executable by the one or more processors to, in response to determining that the predicted change in behavioral health symptomatology satisfies the second threshold, provide one or more recommended interventions to the entity treating the individual.

20. The non-transitory computer-readable medium of claim 19, further comprising program code that is executable by the one or more processors to transmit content to a digital device of the individual, the content comprising coaching regarding strategies to remediate the predicted change.

* * * * *